United States Patent
To

(10) Patent No.: US 10,376,346 B2
(45) Date of Patent: Aug. 13, 2019

(54) DENTAL CLEANING TOOL WITH INTEGRATED SHIELD

(71) Applicant: World Wide Daily Holdings Company Limited, Hong Kong (CN)

(72) Inventor: Chun Yuen To, Hong Kong (CN)

(73) Assignee: World Wide Daily Holdings Company Limited, Hong Kong (CN)

(*) Notice: Subject to any disclaimer, the term of this patent is extended or adjusted under 35 U.S.C. 154(b) by 0 days.

(21) Appl. No.: 16/054,313

(22) Filed: Aug. 3, 2018

(65) Prior Publication Data

US 2019/0083213 A1  Mar. 21, 2019

Related U.S. Application Data

(63) Continuation of application No. PCT/CN2017/102246, filed on Sep. 19, 2017.

(51) Int. Cl.
*A61C 15/04* (2006.01)
*A61C 15/02* (2006.01)
*A46B 15/00* (2006.01)

(52) U.S. Cl.
CPC .......... *A61C 15/046* (2013.01); *A61C 15/02* (2013.01); *A61C 15/041* (2013.01); *A46B 15/0069* (2013.01); *A46B 2200/108* (2013.01)

(58) Field of Classification Search
CPC ..... A61C 15/046; A61C 15/02; A61C 15/041; A61C 15/04; A46B 2200/108; A61K 8/046
See application file for complete search history.

(56) References Cited

U.S. PATENT DOCUMENTS

2012/0111348 A1* 5/2012 Prokopchuk .......... A61C 15/02
132/200

FOREIGN PATENT DOCUMENTS

| CN | 201558187 U | 8/2010 |
|---|---|---|
| CN | 201631405 U | 11/2010 |
| CN | 202223372 U | 5/2012 |
| CN | 205286573 U | 6/2016 |
| CN | 205339184 U | 6/2016 |

(Continued)

OTHER PUBLICATIONS

Machine Translation of WorldWide Stationary CN # 106491227 document Provided with IDS of Aug. 3, 2018.*

(Continued)

*Primary Examiner* — Tatiana L Nobrega
*Assistant Examiner* — Brianne E Kalach
(74) *Attorney, Agent, or Firm* — Armstrong Teasdale LLP

(57) ABSTRACT

A dental cleaning tool includes a body portion defining a longitudinal axis of the dental cleaning tool. The body portion includes a floss assembly including a first arm and a second arm extending substantially perpendicularly relative to the longitudinal axis, a receiving slot formed in the first arm, and a shield formed on the first arm. The shield is configured to cover the receiving slot such that access to the receiving slot is restricted from a first direction. The tool also includes a secondary cleaning tool coupled to the first arm. The secondary cleaning tool is pivotable relative to the first arm in at least two degrees of freedom such that the secondary cleaning tool is insertable into the receiving slot from a second direction different than the first direction.

20 Claims, 8 Drawing Sheets

(56) References Cited

FOREIGN PATENT DOCUMENTS

CN          106491227  A    3/2017
WO       2012116451  A1    9/2012

OTHER PUBLICATIONS

International Search Report issued in PCT/CN2017/102246 dated Jun. 6, 2018.
Written Opinion issued in PCT/CN2017/102246 dated Jun. 6, 2018.

* cited by examiner

DENTAL CLEANING TOOL WITH INTEGRATED SHIELD

CROSS-REFERENCE TO RELATED APPLICATIONS

This application is a continuation of International Patent Application No. PCT/CN2017/102246, filed Sep. 19, 2017, and is hereby incorporated by reference in its entirety.

FIELD

The field of this disclosure relates generally to dental cleaning tools and, more specifically, to a dental cleaning tool having a secondary cleaning tool and a shield that partially covers a receiving slot configured to selectively stow the secondary cleaning tool therein.

BACKGROUND

Dental cleaning tools are used to remove food remnants and/or build-up from the surface of or between teeth. As a result, some known dental cleaning tools include a brush for cleaning the surface of teeth, and other known dental cleaning tools include floss and/or a pick for removing or loosening food remnants (or other debris) from between the user's teeth. Moreover, at least some known dental cleaning tools include a cleaning instrument that is moveable between a deployed position when in use and a stowed position when being stored within the tool. However, many known dental cleaning tools implement bulky and complex mechanical means for shielding the cleaning instrument when in the stowed position. In addition, the cleaning instrument may be an independent component separate from the dental cleaning tools such that the cleaning instrument may be lost when deployed from the dental cleaning tools.

As such, there is a need for a simple and cost effective dental cleaning tool having a secondary cleaning tool moveable between a deployed position and a stowed position, wherein the secondary cleaning tool is disposed within a slot and shielded by a portion of the dental cleaning tool.

BRIEF DESCRIPTION

In one aspect, a dental cleaning tool is provided. The tool generally comprises a body portion defining a longitudinal axis of the dental cleaning tool. The body portion includes a floss assembly having a first arm and a second arm extending substantially perpendicularly relative to the longitudinal axis, a receiving slot formed in the first arm, and a shield formed on the first arm. The shield is configured to cover the receiving slot such that access to the receiving slot is restricted from a first direction. The tool also includes a secondary cleaning tool coupled to the first arm. The secondary cleaning tool is pivotable relative to the first arm in at least two degrees of freedom such that the secondary cleaning tool is insertable into the receiving slot from a second direction different than the first direction.

In another aspect, a dental cleaning tool is provided. The tool generally comprises a body portion defining a longitudinal axis of the dental cleaning tool. The body portion includes a floss assembly having a first arm and a second arm extending substantially perpendicularly relative to the longitudinal axis. A receiving slot is formed in the first arm, wherein the receiving slot defines a shield from a portion of the first arm. The shield is configured to cover the receiving slot such that access to the receiving slot is restricted from a first direction. The tool also includes a secondary cleaning tool coupled to the first arm. The secondary cleaning tool is pivotable relative to the first arm in at least two degrees of freedom such that the secondary cleaning tool is insertable into the receiving slot from a second direction different than the first direction.

In yet another aspect, a dental cleaning tool is provided. The tool generally comprises a body portion defining a longitudinal axis of the dental cleaning tool. The body portion includes a floss assembly including a first arm and a second arm extending substantially perpendicularly relative to the longitudinal axis, and a bridge segment extending between the first arm and the second arm. A receiving slot is formed in the first arm and the bridge segment, and a shield is formed on the first arm and the bridge segment. The shield is configured to cover the receiving slot such that access to the receiving slot is at least partially restricted from a first direction. A secondary cleaning tool coupled to the first arm, wherein the secondary cleaning tool is pivotable relative to the first arm in at least two degrees of freedom such that the secondary cleaning tool is insertable into the receiving slot from a second direction different than the first direction.

In still another aspect, a dental cleaning tool generally comprises a body portion defining a longitudinal axis of the dental cleaning tool. The body portion comprises a floss assembly having a first arm and a second arm extending substantially perpendicularly relative to the longitudinal axis. A receiving slot is formed in the first arm. The receiving slot is covered, in part, by a shield extending from a portion of the first arm. A secondary cleaning tool is coupled to the first arm via a living hinge. The secondary cleaning tool is pivotable relative to the first arm about the living hinge in at least two degrees of freedom such that the secondary cleaning tool is insertable into the receiving slot by moving the secondary cleaning tool in at least two directions about the living hinge.

DETAILED DESCRIPTION OF THE DRAWINGS

Figure 1:
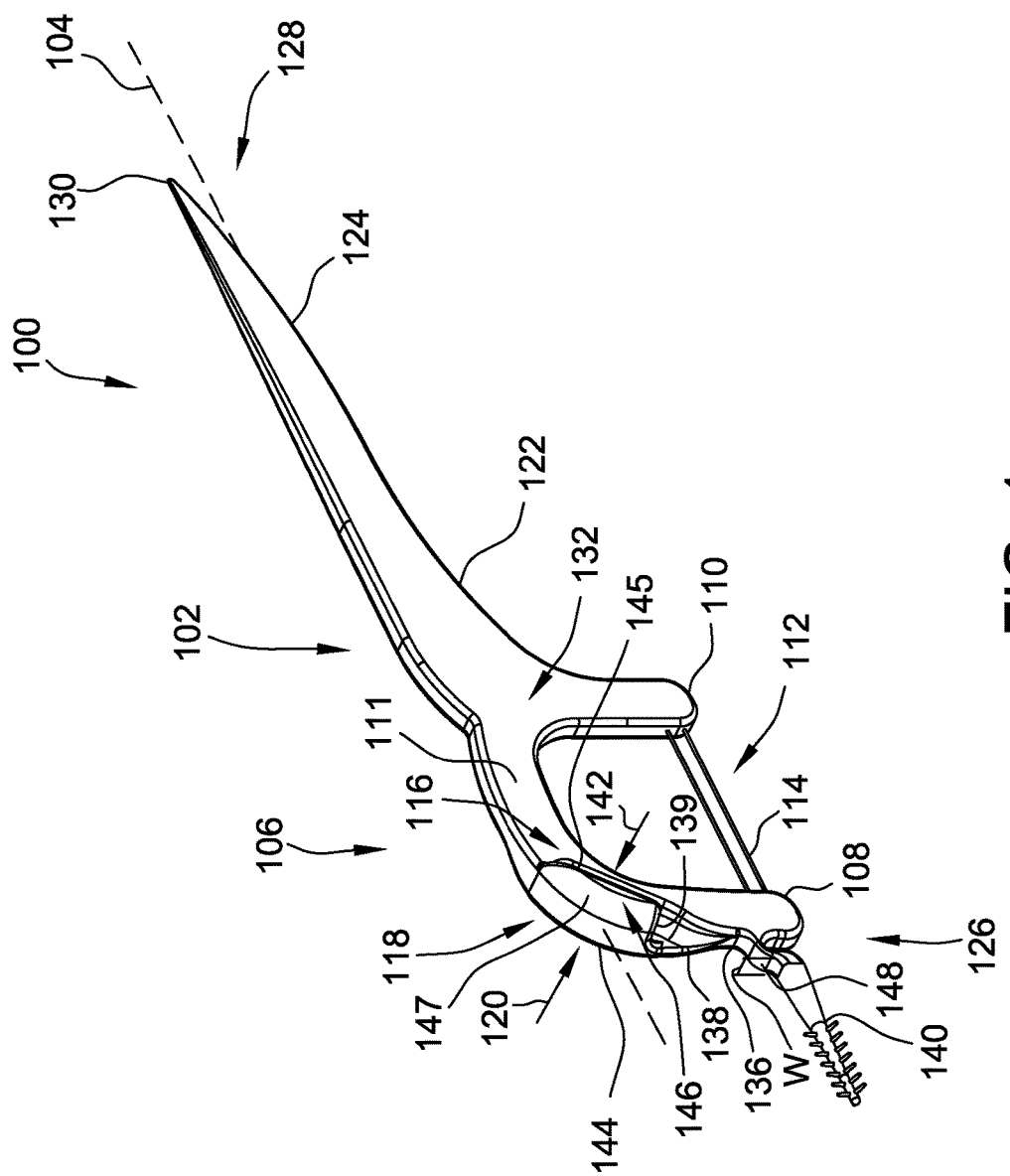
FIG. 1 is a perspective view of one suitable embodiment of a dental cleaning tool of the present disclosure, the dental cleaning tool having a secondary cleaning tool illustrated in the deployed position.

FIGS. 1-4 illustrate one suitable embodiment of a dental cleaning tool, indicated generally at 100, of the present disclosure. As illustrated herein, the dental cleaning tool 100 includes a body portion, indicated generally at 102, defining a longitudinal axis 104 of the dental cleaning tool. The body portion 102 includes a floss assembly, indicated generally at 106, having a first arm 108 and a second arm 110 extending substantially perpendicularly relative to the longitudinal axis 104 of the dental cleaning tool 100. The floss assembly 106 further includes a bridge segment 111 of the body portion 102 that is oriented to extend substantially coaxially with the longitudinal axis 104. The first arm 108 and the second arm 110 are spaced from each other by a distance such that a gap, indicated generally at 112, is defined therebetween. In one embodiment, the dental cleaning tool 100 includes a length of floss 114 that spans the gap 112 and that is coupled between the first arm 108 and the second arm 110. In one suitable embodiment, the floss 114 is held in tension across the gap 112 to facilitate removing or loosening food remnants or other debris when inserted between a user's teeth.

The body portion 102 further includes a receiving slot, indicated generally at 116, formed in the first arm 108, and a shield, indicated generally at 118, formed on the first arm 108 and the bridge segment 111 of the body portion 102. The receiving slot 116 extends along the first arm 108 and the bridge segment 111 of the body portion 102, and the shield 118 is positioned to at least partially cover the receiving slot 116. Moreover, in the example embodiment, the receiving slot 116 is oriented obliquely relative to the longitudinal axis 104. The shield 118 is oriented to restrict access to the receiving slot 116 from a first direction 120, as will be explained in further detail below. In addition, in one embodiment, the first arm 108 and the shield 118 are formed as a monolithic integral structure.

The body portion 102 further includes a handle 122 extending from the floss assembly 106, and a toothpick member 124 extending from the handle 122. The floss assembly 106 is defined at a first end, indicated generally at 126, of the body portion 102, and the toothpick member 124 is defined at a second end, indicated generally at 128, of the body portion 102. The body portion 102 is tapered such that the toothpick member 124 includes a pointed tip 130 at the second end 128 thereof.

In the exemplary embodiment, the body portion 102 includes a first side, indicated generally at 132, and a second side, indicated generally at 134, opposing the first side 132. As shown, the receiving slot 116 is formed in the first arm 108 on the first side 132 of the body portion 102. Moreover, the first arm 108 includes a front face 136 extending between the first side 132 and the second side 134 of the body portion 102. The receiving slot 116 extends along the body portion 102 such that a finger tab opening 138 is defined in the front face 136 of the first arm 108. The finger tab opening 138 is also at least partially defined by a bottom edge 139 of the shield 118. The finger tab opening 138 provides access to the receiving slot 116 to facilitate deployment of a cleaning instrument therefrom, as will be explained in further detail below.

The dental cleaning tool 100 also includes a secondary cleaning tool 140 coupled to the first arm 108. The secondary cleaning tool 140 may be any suitable cleaning instrument that enables the dental cleaning tool 100 to function as described herein. Example secondary cleaning tools include, but are not limited to, a bristled cleaning member and a toothpick member. In the illustrated embodiment, for example, the secondary cleaning tool 140 is a bristled cleaning member. In one suitable embodiment, the secondary cleaning tool 140 is pivotable relative to the first arm 108 in at least two degrees of freedom such that the secondary cleaning tool 140 is insertable into the receiving slot 116 from a second direction 142 different than the first direction 120.

For example, as described above, the shield 118 is oriented to restrict access to the receiving slot 116 from the first direction 120. More specifically, the shield 118 includes a first portion 144 oriented to restrict access to the receiving slot 116 from the first direction 120, and a second portion, indicated generally at 146, oriented to partially restrict access to the receiving slot 116 from a second direction 142. The first portion 144 of the shield 118 is formed on, and extends between, the first arm 108 and the bridge segment 111 of body portion 102. In the example embodiment, the first portion 144 extends arcuately between the first arm 108 and the bridge segment 111 such that a rounded edge is formed on the body portion 102. The first portion 144 also has a width relative a thickness of the body portion 102 such that the second portion 146 is positioned a distance from the first side 132 of the body portion 102, which necessitates the secondary cleaning tool 140 to be pivotable relative to the first arm 108 in at least two degrees of freedom to be insertable into the receiving slot 116.

The second portion 146 of the shield 118 is oriented generally perpendicular relative to the first portion 144 such that the shield 118 extends over the receiving slot 116. For example, in one embodiment, the second portion 146 includes a rounded edge 147 positioned proximate to the first portion 144. The rounded edge 147 provides a contour to the shield 118 such that the second portion 146 is oriented perpendicularly relative to the first portion 144. The second portion 146 extends a distance from the first portion 144 and is oriented such that the receiving slot 116 is partially exposed when viewed from the first side 132 of the body portion 102. More specifically, the second portion 146 includes a side edge 145 oriented obliquely relative to the longitudinal axis 104 of the body portion 102. In one embodiment, the second portion 146 extends a distance from the first portion 144 such that, when viewed from the first side 132 of the body portion 102, the side edge 145 extends across the receiving slot 116 from the first arm portion 108 to the bridge segment 111. As such, the shield 118 facilitates restricting access by the secondary cleaning tool 140 to the receiving slot 116 when in the deployed position, and facilitates retaining the secondary cleaning tool 140 within the receiving slot 116 when in the stowed position. The shield 118 also facilitates protecting the secondary cleaning tool 140 when in the stowed position.

In one suitable embodiment, a bendable tab 148 (e.g., a living hinge) extends between the body portion 102 and the secondary cleaning tool 140. The bendable tab 148 is dimensioned such that the secondary cleaning tool 140 is pivotable in a first degree of freedom 149 (shown in FIG. 3) when a first force is applied thereto, and such that the secondary cleaning tool 140 is pivotable in a second degree of freedom 151 (shown in FIG. 2) when a second force, greater than the first force, is applied thereto. For example, the bendable tab 148 has a width W (shown in FIG. 1) and a thickness T (shown in FIG. 4), and the width W is greater than the thickness T. As such, the bendable tab 148 is dimensioned such that the secondary cleaning tool 140 is stowable within, or deployable from, the receiving slot 116 in a deliberate and intentional manner. That is, the secondary cleaning tool 140 can be manually moved by a user about the bendable tab 148 to selectively move the secondary cleaning tool between the stowed and deployed positions.

Figure 2:
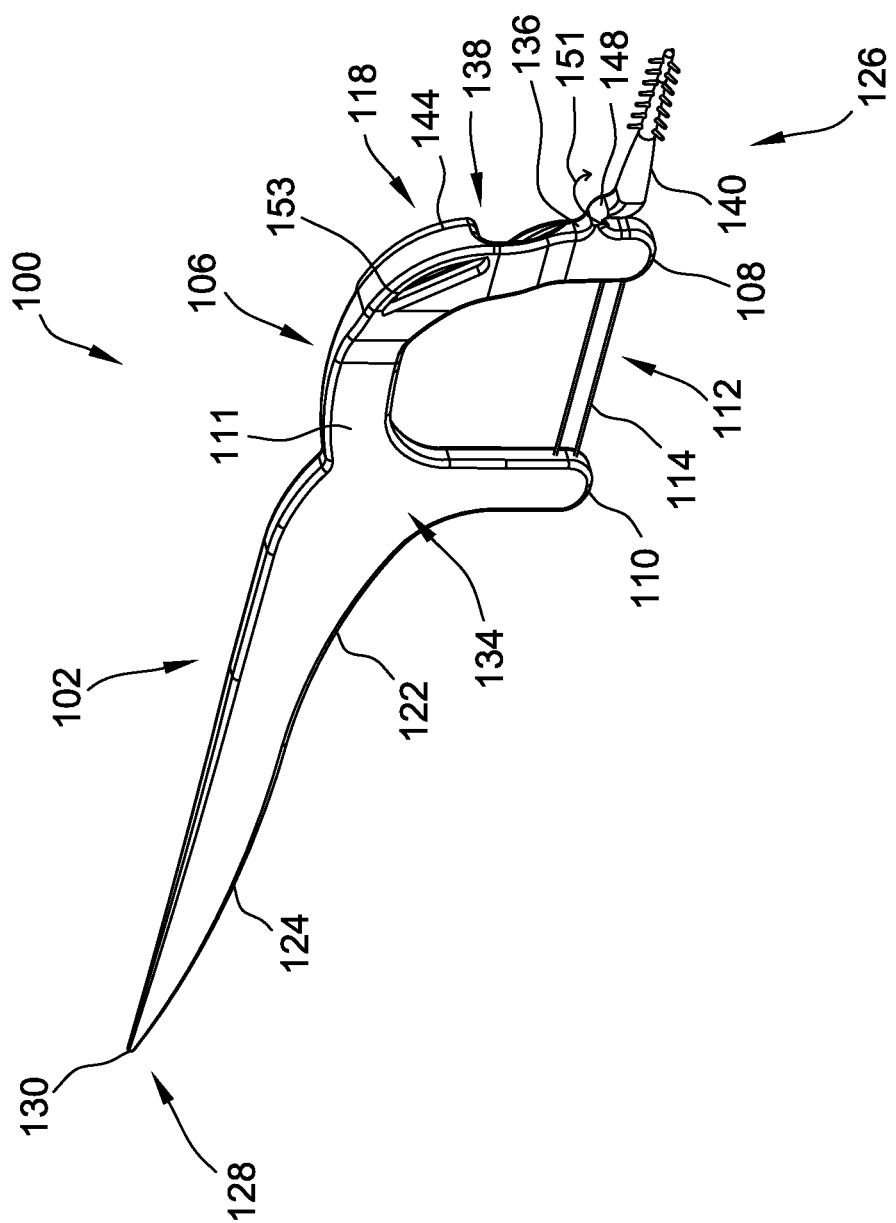
FIG. 2 is another perspective view of the dental cleaning tool seen in FIG. 1.

Referring to FIG. 2, the floss assembly 106 further includes a side opening 153 defined on the second side 134 of the body portion 102. The side opening 153 provides a viewing window to the interior of the receiving slot 116 from the second side 134, such that a user of the dental cleaning tool 100 can see whether the secondary cleaning tool 140 is stowed within the receiving slot 116, thereby increasing the aesthetic appeal of, and facilitating interest in, the dental cleaning tool 100 to the user.

Figure 3:
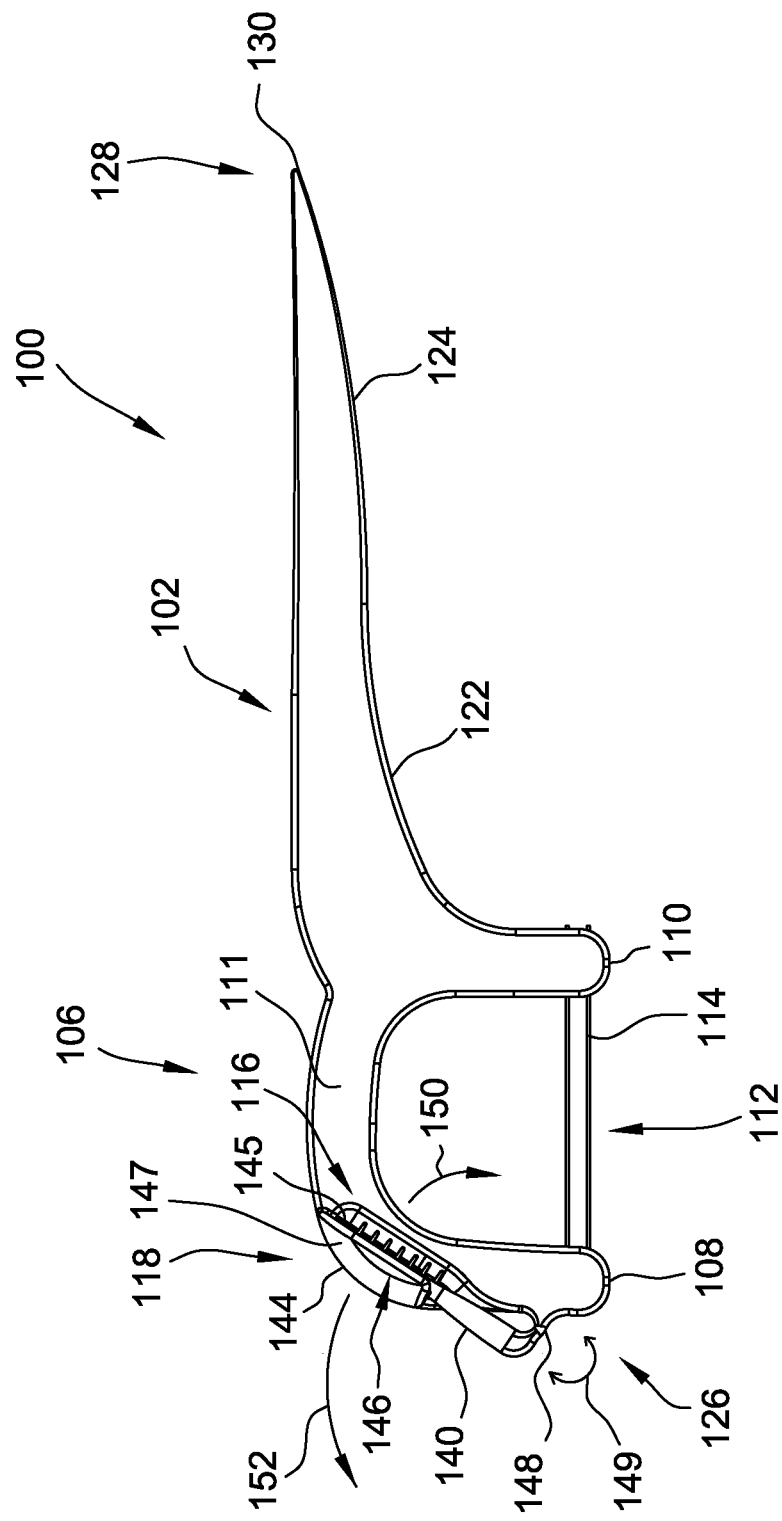
FIG. 3 is a side view of the dental cleaning tool seen in FIG. 1, the secondary cleaning tool being illustrated in a stowed position.
Figure 4:
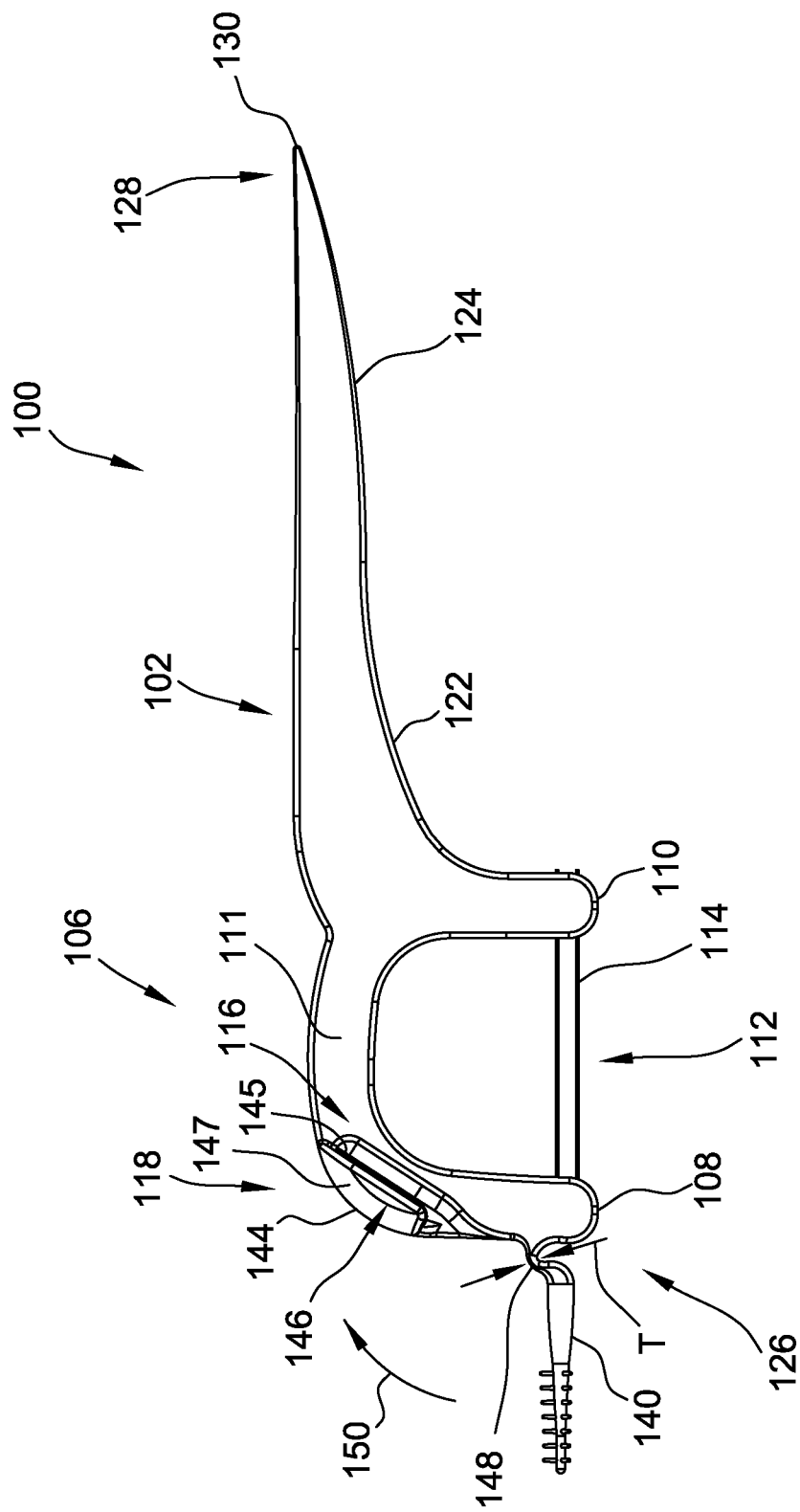
FIG. 4 is a side view of the dental cleaning tool similar to FIG. 3 but illustrating the secondary cleaning tool in the deployed position.
Figure 5:
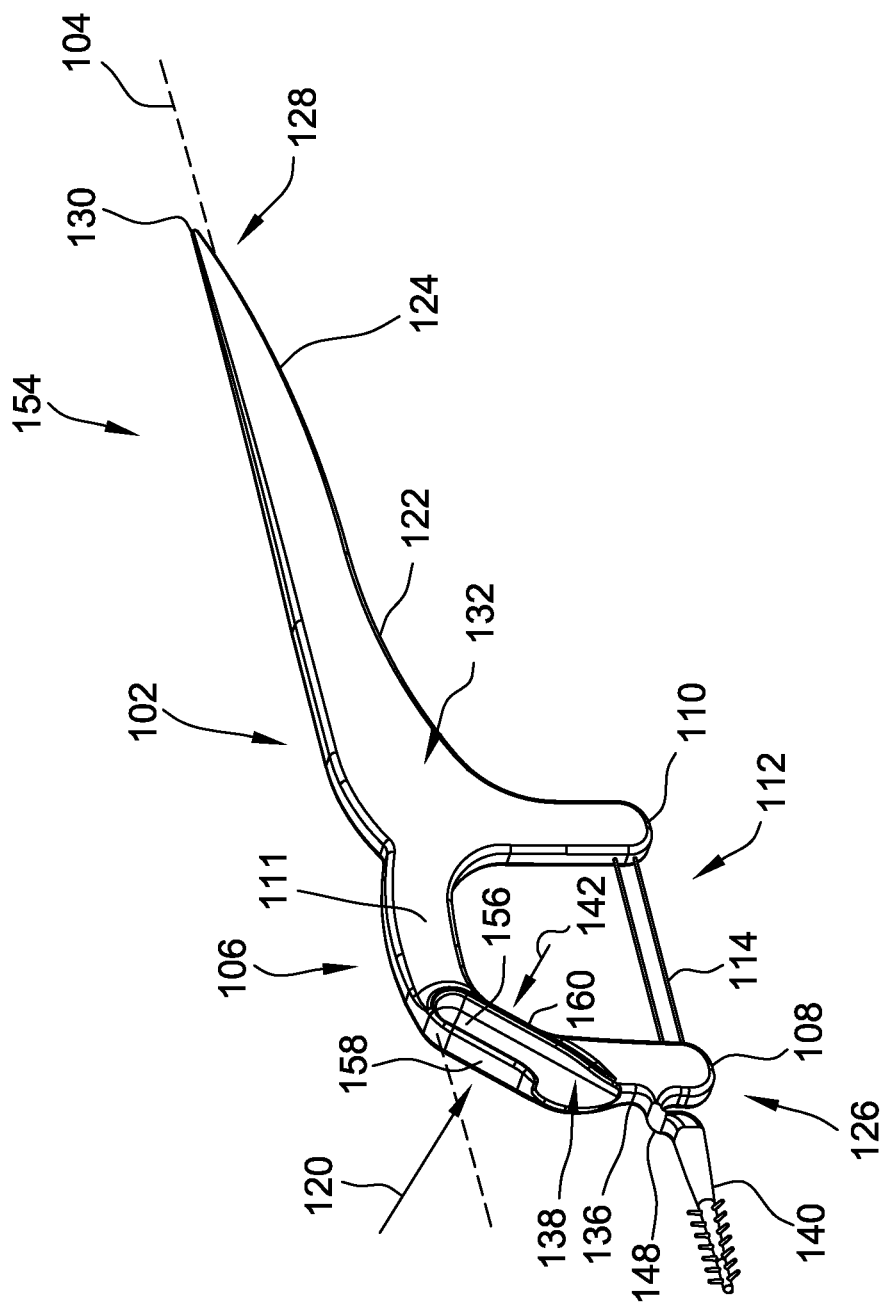
FIG. 5 is a perspective view of another suitable embodiment of a dental cleaning tool of the present disclosure, the dental cleaning tool having a secondary cleaning tool illustrated in the deployed position.

With reference to FIGS. 3 and 4, the secondary cleaning tool 140 is selectively manually pivotable relative to the first arm 108 for positioning the secondary cleaning tool in either the stowed position (shown in FIG. 3) or the deployed position (shown in FIG. 4). In operation, the secondary cleaning tool 140 is deployed from the stowed position by accessing the secondary cleaning tool 140 via the finger tab opening 138 to release the secondary cleaning tool 140 from underneath the shield 118. More specifically, a user may manually grasp and pivot the secondary cleaning tool 140 in a first rotational direction 150, pivot the secondary cleaning tool 140 away from the first side 132 of the body portion 102, and then pivot the secondary cleaning tool 140 in a second rotational direction 152 to deploy the secondary cleaning tool 140. To stow the secondary cleaning tool 140 from the deployed position, a user may manually grasp and pivot the secondary cleaning tool 140 in the first rotational direction 150, pivot the secondary cleaning tool 140 away from the first side 132 of the body portion 102 such that the secondary cleaning tool 140 clears the shield 118 when rotating in the first rotational direction 150, and then pivoting the secondary cleaning tool 140 towards the first side 132 of the body portion 102 such that the secondary cleaning tool 140 is inserted within the receiving slot 116.

FIGS. 5-8 illustrate another suitable embodiment of a dental cleaning tool 154 of the present disclosure. The dental cleaning tool 154 is substantially similar to the dental cleaning tool 100 shown in FIGS. 1-4 and, accordingly, like numerals are used to refer to like elements of both dental cleaning tools 100 and 154.

In the exemplary embodiment, the body portion 102 includes a receiving slot, indicated generally at 156, formed in the first arm 108. The receiving slot 156 is at least partially covered by a shield 158 extending from a portion of the first arm 108. The shield 158 is oriented to restrict access to the receiving slot 156 from the first direction 120. More specifically, the shield 158 is oriented obliquely relative to the longitudinal axis 104 of the body portion 102. In addition, the receiving slot 156 defines a side opening 160 on the first side 132 of the body portion 102. The side opening 160 provides unimpeded access to the receiving slot 156 from the second direction 142.

Figure 7:
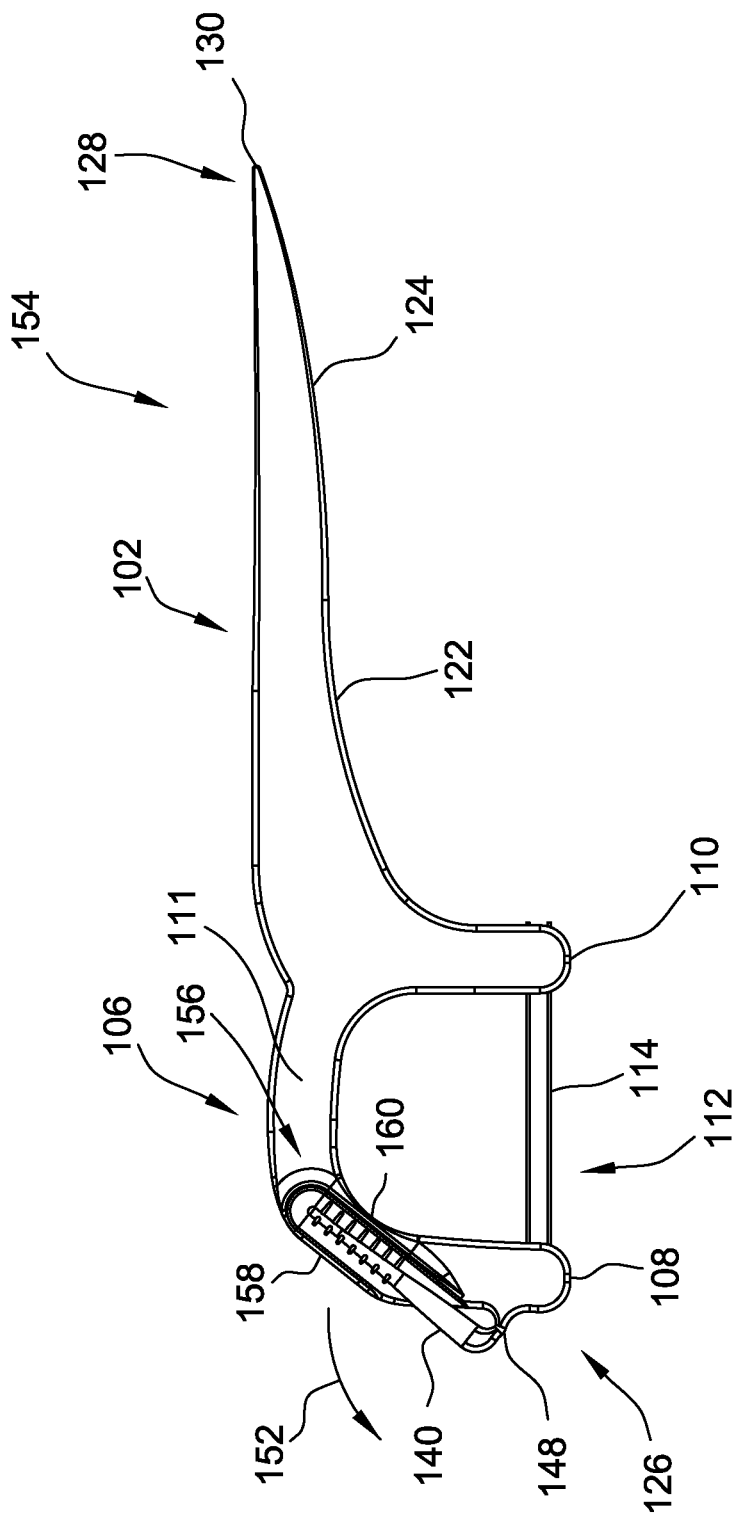
FIG. 7 is a side view of the dental cleaning tool seen in FIG. 5, the secondary cleaning tool being illustrated in a stowed position.
Figure 8:
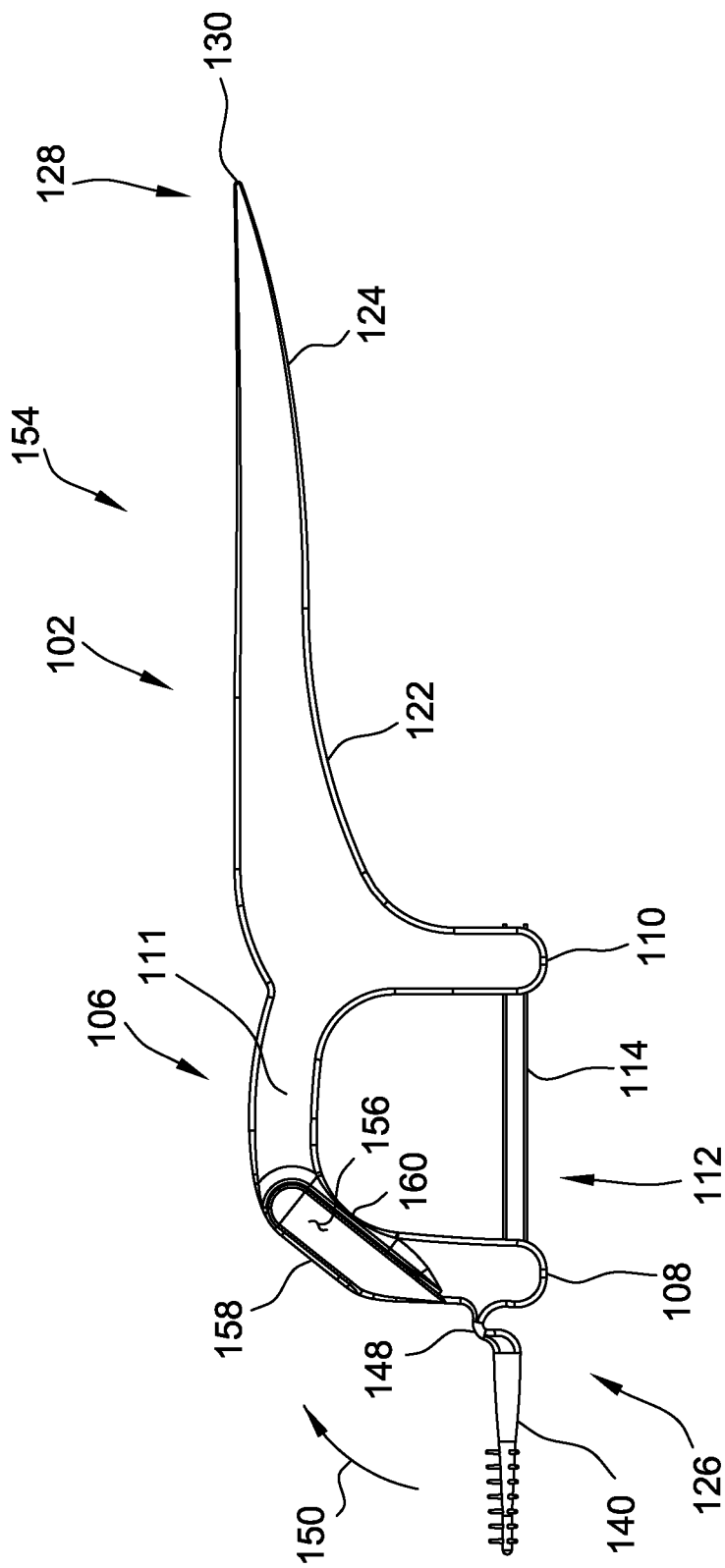
FIG. 8 is a side view of the dental cleaning tool similar to FIG. 7 but illustrating the secondary cleaning tool in the deployed position.

As illustrated in FIGS. 7 and 8, the receiving slot 156 extends along the first arm 108 and the bridge segment 111 of the body portion 102, and the shield 118 is positioned to at least partially cover the receiving slot 156. Similar to the shield 118 (shown in FIGS. 1-4), the shield 158 is formed on, and extends between, the first arm 108 and the bridge segment 111 of the body portion 102. In one suitable embodiment, the shield 158 extends linearly between the first arm 108 and the bridge segment 111. The shield 158 also has a width greater than a thickness of the body portion 102 that necessitates the secondary cleaning tool 140 to be pivotable relative to the first arm 108 in at least two degrees of freedom to be insertable into the receiving slot 116.

Figure 6:
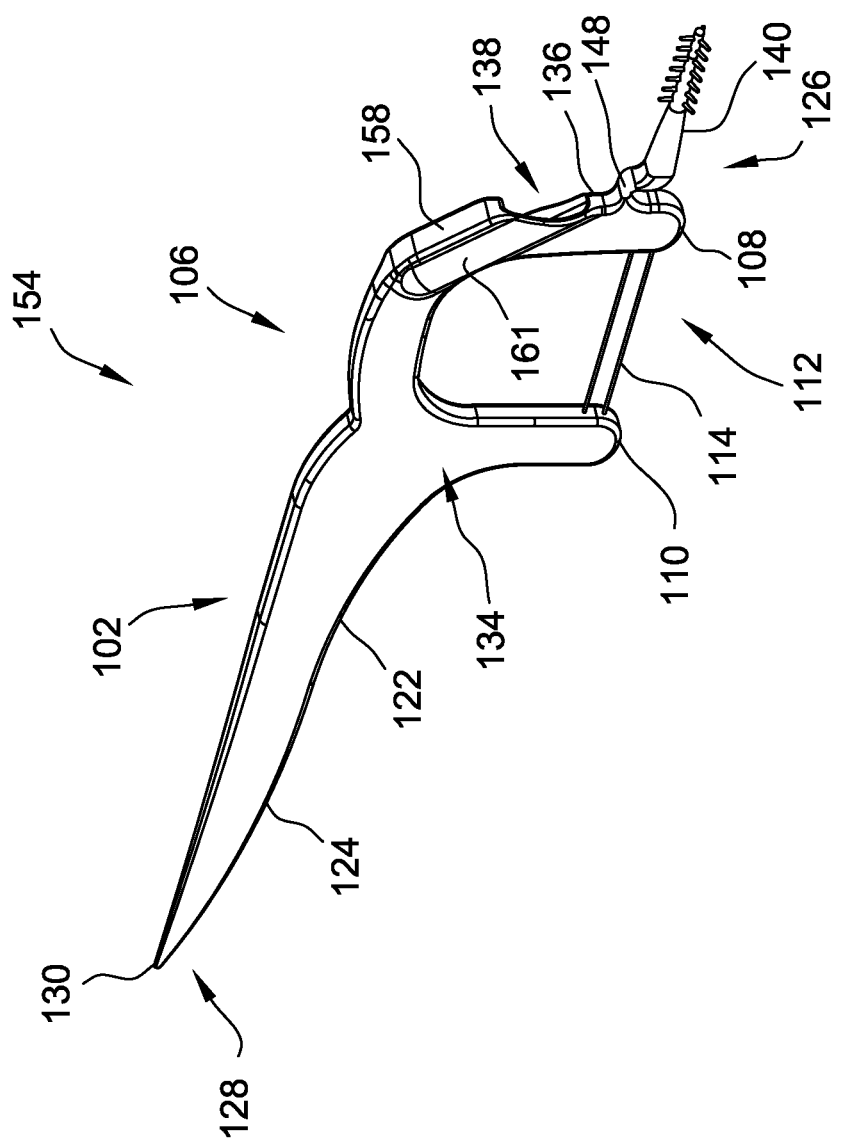
FIG. 6 is another perspective view of the dental cleaning tool seen in FIG. 5.

In addition, referring now to FIG. 6, the body portion 102 includes a bulged side wall 161 formed on the second side 134 thereof. The bulged side wall 161 extends between the first arm 108 and the bridge segment 111 of the body portion 102, and extends outward from the second side 134 of the body portion 102 such that a volume of the receiving slot 156 is increased.

Referring again to FIGS. 7 and 8, the secondary cleaning tool 140 is selectively pivotable relative to the first arm 108 for positioning in either the stowed position (shown in FIG. 7) or the deployed position (shown in FIG. 8). In operation, the secondary cleaning tool 140 is manually deployed from the stowed position by accessing the secondary cleaning tool 140 via the finger tab opening 138. More specifically, a user manually grasps and pivots the secondary cleaning tool 140 away from the first side 132 of the body portion 102 to clear the shield 158, and then pivots the secondary cleaning tool 140 in the second rotational direction 152 to deploy the secondary cleaning tool 140. To stow the secondary cleaning tool 140 from the deployed position, a user manually grasp and pivot the secondary cleaning tool 140 in the first rotational direction 150, pivot the secondary cleaning tool 140 away from the first side 132 of the body portion 102 such that the secondary cleaning tool 140 clears the shield 158 when rotating in the first rotational direction 150, and then pivoting the secondary cleaning tool 140 towards the first side 132 of the body portion 102 such that the secondary cleaning tool 140 is inserted within the receiving slot 156.

In suitable embodiments, the dental cleaning tool 100 of FIGS. 1-4 and/or the dental cleaning tool 154 of FIGS. 5-8 may be formed in any suitable manner and of any suitable material. For example, the dental cleaning tools 100, 154 may be formed from metal, wood, plastic, and/or combinations thereof. In one preferred embodiment, the dental cleaning tools 100 and 154 are molded or otherwise formed from a single piece of resilient synthetic material, such as, but not limited to, plastic or metal.

The dental cleaning tools described herein include a shield and a receiving slot formed on a first arm of a floss assembly, and a secondary cleaning tool coupled to the first arm and selectively stowable or deployed from the receiving slot. The shield facilitates retaining the secondary cleaning tool within the receiving slot when in the stowed position, and restricts access to the receiving slot when the secondary cleaning tool is in the deployed position. As such, the secondary cleaning tool is restricted from being unintentionally deployed from the stowed position, or from being unintentionally stowed from the deployed position. Moreover, when in the stowed position, the secondary cleaning tool is integrated with the first arm such that use of the floss assembly remains unimpeded.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the disclosure, it is intended that all matter contained in the above description and shown in the accompanying drawings shall be interpreted as illustrative and not in a limiting sense.

This written description uses examples to describe the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A dental cleaning tool comprising:
   a body portion defining a longitudinal axis of the dental cleaning tool, wherein the body portion comprises:
   a handle for gripping the dental cleaning tool,
   a floss assembly having a bridge segment coupled to the handle, the floss assembly comprising a first arm and a second arm extending from the bridge segment and substantially perpendicularly relative to the longitudinal axis, each arm having opposing upper and lower surfaces and first and second lateral surfaces extending between the upper and lower surfaces, wherein the first lateral surfaces of the first and second arms face one another and a floss extends between the first lateral surfaces of the first and second arms;
   a receiving slot extending through the upper surface of the first arm, a portion of the second lateral surface of the first arm, and a portion of the bridge segment such that the second lateral surface of the first arm is open at a distal end of the slot and the slot is closed at a proximal end opposite the open distal end, the slot defining two interior side surfaces disposed between the open distal end and the closed proximal end; and
   a shield extending a length of the slot between the distal and proximal ends thereof, where the shield extends upwardly and laterally inward to cover at least a portion of the slot; and
   an elongate secondary cleaning tool coupled to the second lateral surface of the first arm, wherein the secondary cleaning tool is pivotable relative to the first arm in at least two degrees of freedom,
   wherein the secondary cleaning tool is configured to be rotated and inserted into the receiving slot to define a non-use position where the secondary cleaning tool is retained by the slot and the shield, and is configured to be rotated out of the slot into a use position where the secondary cleaning tool extends outwardly from the floss assembly.

2. The dental cleaning tool in accordance with claim 1 further comprising a bendable tab extending between the body portion and the secondary cleaning tool.

3. The dental cleaning tool in accordance with claim 2, wherein the bendable tab is dimensioned such that the secondary cleaning tool is pivotable in a first degree of freedom when a first force is applied thereto, and such that the secondary cleaning tool is pivotable in a second degree of freedom when a second force, greater than the first force, is applied thereto.

4. The dental cleaning tool in accordance with claim 1, wherein the shield comprises a first portion oriented to restrict access to the receiving slot from g first direction, and a second portion oriented to partially restrict access to the receiving slot from a second direction.

5. The dental cleaning tool in accordance with claim 4, wherein the first portion of the shield extends arcuately along the first arm, and the second portion of the shield is oriented perpendicularly relative to the first portion.

6. The dental cleaning tool in accordance with claim 1, wherein the first arm and the shield are formed as a monolithic integral structure.

7. The dental cleaning tool in accordance with claim 1, wherein the body portion comprises a first side and a second side opposing the first side, the receiving slot extending along the first side of the body portion.

8. The dental cleaning tool in accordance with claim 7, wherein the first arm comprises a front face extending between the first side and the second side of the body portion, the receiving slot extending along the body portion such that a finger tab opening is defined in the front face.

9. The dental cleaning tool in accordance with claim 1, wherein the body portion further comprises a handle extending from the floss assembly and a toothpick member extending from the handle.

10. The dental cleaning tool in accordance with claim 1, wherein the secondary cleaning tool comprises a bristled cleaning member.

11. A dental cleaning tool comprising:
    a body portion defining a longitudinal axis of the dental cleaning tool, wherein the body portion comprises:
    a floss assembly having a bridge segment, the floss assembly further comprising a first arm and a second arm extending from the bridge segment and substantially perpendicularly relative to the longitudinal axis, each arm having opposing upper and lower surfaces and first and second lateral surfaces extending between the upper and lower surfaces wherein the first lateral surfaces of the first and second arms face one another and a floss extends between the first lateral surfaces of the first and second arms; and
    a receiving slot extending through at least one of the upper surface of the first arm, a portion of the second lateral surface of the first arm, and a portion of the bridge segment, the receiving slot defining two interior side surfaces disposed between distal and proximal ends of the receiving slot, the receiving slot at least partially covered by a shield extending a length of the receiving slot between the distal and proximal ends thereof and extending upwardly and laterally inward; and
    an elongate secondary cleaning tool coupled to the second lateral surface of the first arm, wherein the secondary cleaning tool is pivotable relative to the first arm in at least two degrees of freedom,
    wherein the secondary cleaning tool is configured to be rotated and inserted into the receiving slot to define a non-use position where the secondary cleaning tool is retained by the receiving slot and the shield, and is configured to be rotated out of the receiving slot into a use position where the secondary cleaning tool extends outwardly from the floss assembly.

12. The dental cleaning tool in accordance with claim 11 further comprising a bendable tab extending between the body portion and the secondary cleaning tool.

13. The dental cleaning tool in accordance with claim 12, wherein the bendable tab is dimensioned such that the secondary cleaning tool is pivotable in a first degree of freedom when a first force is applied thereto, and such that the secondary cleaning tool is pivotable in a second degree of freedom when a second force, greater than the first force, is applied thereto.

14. The dental cleaning tool in accordance with claim 11, wherein the shield is oriented obliquely relative to the longitudinal axis of the body portion.

15. The dental cleaning tool in accordance with claim 11, wherein the first arm and the shield are formed as a monolithic integral structure.

16. The dental cleaning tool in accordance with claim 11, wherein the body portion comprises a first side and a second side opposing the first side, the receiving slot extending along the first side of the body portion.

17. The dental cleaning tool in accordance with claim 16, wherein the receiving slot defines a side opening on the first side of the body portion, the side opening providing access to the receiving slot from a second direction.

18. The dental cleaning tool in accordance with claim 16, wherein the first arm comprises a front face extending between the first side and the second side of the body portion, the receiving slot extending along the body portion such that a finger tab opening is defined in the front face.

19. The dental cleaning tool in accordance with claim 11, wherein the body portion further comprises a handle extending from the floss assembly and a toothpick member extending from the handle.

20. A dental cleaning tool comprising:
a body portion defining a longitudinal axis of the dental cleaning tool, wherein the body portion comprises:
a floss assembly having a bridge segment, the floss assembly further comprising a first arm and a second arm extending from the bridge segment and substantially perpendicularly relative to the longitudinal axis, each arm having opposing upper and lower surfaces and first and second lateral surfaces extending between the upper and lower surfaces, wherein the first lateral surfaces of the first and second arms face one another and a floss extends between the first lateral surfaces of the first and second arms; and
a receiving slot extending through the upper surface of the first arm, a portion of the second lateral surface of the first arm, and a portion of the bridge segment such that the second lateral surface of the first arm is open at a distal end of the receiving slot and the receiving slot is closed at a proximal end opposite the open distal end, the receiving slot defining two interior side surfaces disposed between the open distal end and the closed proximal end, the receiving slot being covered, at least in part, by a shield extending a length of the receiving slot between the distal and proximal ends thereof and extending upwardly and laterally inward to cover at least a portion of the receiving slot; and
an elongate secondary cleaning tool coupled to the second lateral surface of the first arm via a living hinge, the secondary cleaning tool being pivotable relative to the first arm about the living hinge in at least two degrees of freedom,
wherein the secondary cleaning tool is configured to be rotated and inserted into the receiving slot to define a non-use position where the secondary cleaning tool is retained by the receiving slot and the shield, and is configured to be rotated out of the receiving slot into a use position where the secondary cleaning tool extends outwardly from the floss assembly.

* * * * *